United States Patent
Emmrich

[11] Patent Number: 5,961,468
[45] Date of Patent: Oct. 5, 1999

[54] DETECTION OF THE HEART RESPONSE OF PACEMAKER PATIENTS

[75] Inventor: Thomas Emmrich, Gaertringen, Germany

[73] Assignee: Hewlett-Packard Company, Palo Alto, Calif.

[21] Appl. No.: 09/044,727

[22] Filed: Mar. 19, 1998

[30] Foreign Application Priority Data

May 12, 1997 [EP] European Pat. Off. ............. 97107707

[51] Int. Cl.⁶ ................................................ A61B 5/0402
[52] U.S. Cl. ............................................................ 600/510
[58] Field of Search ................................... 600/509, 510, 600/519, 521, 523

[56] References Cited

U.S. PATENT DOCUMENTS 4,537,201  8/1985  Delle-Vedove et al. .
5,184,615  2/1993  Nappholz et al. .

FOREIGN PATENT DOCUMENTS

0105784A1  9/1983  European Pat. Off. .

OTHER PUBLICATIONS

European Search Report, EP 97 10 7707, Oct. 21, 1997.

*Primary Examiner*—William E. Kamm
*Assistant Examiner*—George R. Evanisko

[57] ABSTRACT

The detection of a heart response in an ECG signal of a patient having a pacemaker emitting a pace pulse. An area of a pulse of the ECG signal comprising a pace pulse tail of the pace pulse is first determined and an estimated mathematical function is derived from the determined area. The estimated mathematical function and the ECG signal are evaluated together in order to distinguish the heart response in the ECG signal.

12 Claims, 4 Drawing Sheets

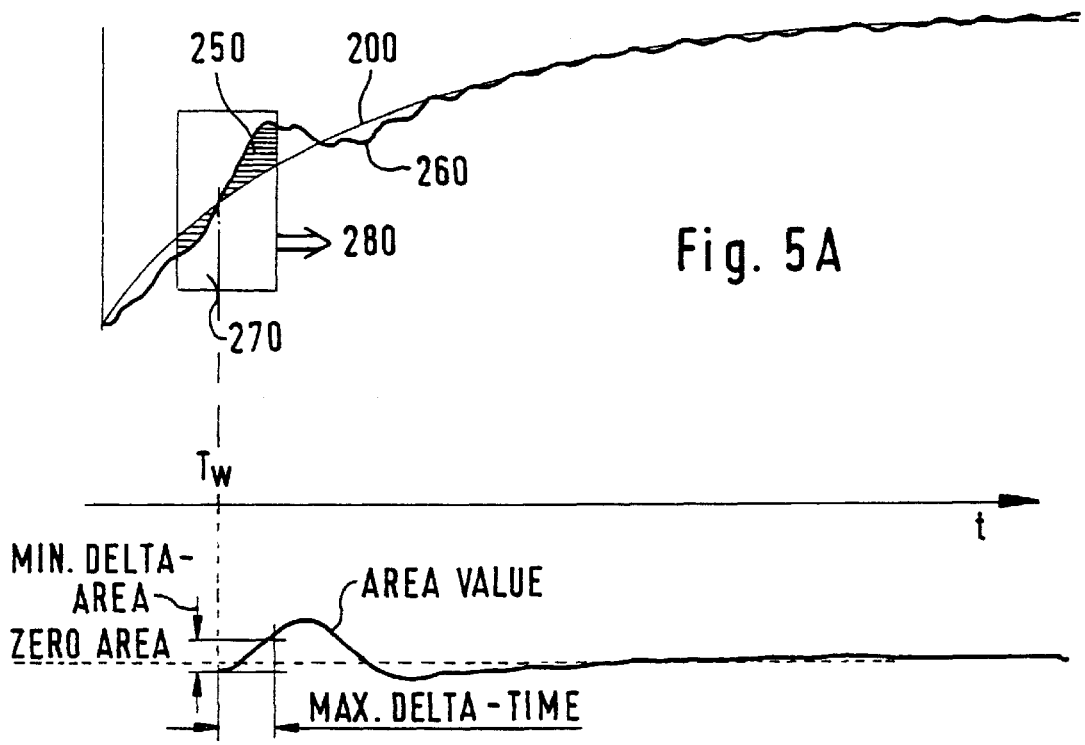
Fig. 5A
Fig. 5B
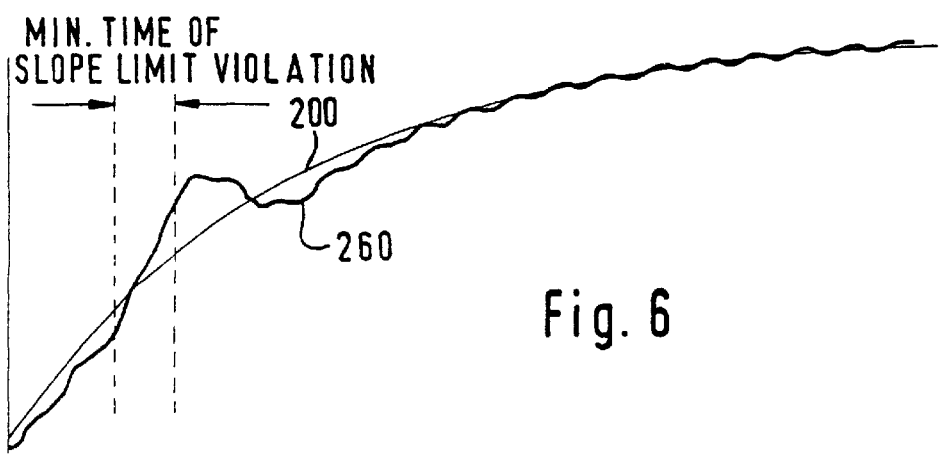
Fig. 6

DETECTION OF THE HEART RESPONSE OF PACEMAKER PATIENTS

BACKGROUND OF THE INVENTION

The present invention generally relates to the detecting of a heart response in an ECG signal of a patient having a pacemaker emitting a pace pulse.

In any Electrocardiogram (ECG) monitoring device, an important feature is the detection and characterization of each individual heart beat present in the ECG signal. This information is then used to generate both heart rate information and alarms in life threatening situations. Monitoring an ECG signal from a patient having a pacemaker is difficult as pace pulses generated by the pacemaker can occur at any time. When they occur between QRS complexes, they can be incorrectly detected by a QRS detector and result in an incorrect high heart rate measurement. When they occur during a QRS complex, they can cause incorrect feature measurement and result in an erroneous QRS classification. In particular, the detection of asystole is necessary to alert nurses of the cessation of heart response which is indicated by the absence of the QRS complex in the ECG signal. However, in the case of patients with pacemakers, the ECG signal, even after asystole, contains periodically occurring pace pulses, which may resemble heart response. The presence of pace pulses on an ECG signal makes it difficult to detect such asystole conditions.

FIG. 1A shows a typical pace pulse 10 consisting of two components, a main pulse 20 and pace pulse tail 30, sometimes also referred to as a re-polarization pulse. The main pulse 20, which is used to stimulate the heart, is characterized by its narrow width, sharp rise and fall, and large variation in amplitude. The actual shape of the pace pulse 10 mainly depends on the output coupling design of the pacemaker. The pace pulse tail 30 is used to deplete the capacitive coupling generated by the delivery of the pace pulse charge built up between the heart and the pacemaker. The shape and size of the pace pulse tail 30 are a function of the energy content of the pace pulse tail 20 and the amount of capacitive coupling. In addition to re-polarization, bandpass filtering in the monitoring equipment may create a further portion to the pace pulse tail 30.

FIG. 1B shows an example of a shape of a heart response 40. The heart response 40—also referred to as QRS complex—represents the response of the heart onto the stimulating pace pulse 10.

FIG. 1C shows an example of a shape of an actual ECG signal 50 which results from the pace pulse 10 superimposed with the heart response 40 of the patient. In other words, the synthetic pace pulse 10 stimulates the patient's heart response 40, which is superimposed with the pace pulse 10 to the ECG signal 50 to be measured by the ECG monitoring device. The ECG signal 50 comprises a positive pulse 60, mainly determined by the main pulse 20, and a negative pulse 70, mainly determined by the pace pulse tail 30 and the heart response 40.

Some pacemakers generate a pace pulse tail 30 with a substantially exponential decay (as indicated in FIG. 1A). In order to more accurately monitor ECG signals, it has been found helpful to eliminate pace pulse signals from the pacemaker. However, such elimination requires that the pace pulse 10 is first identified. It has been particularly found difficult to detect the heart response 40 on the pace pulse tail 30, especially if the energy delivered by the pacemaker is high. For a real-time system like a patient monitor, it is difficult to distinguish the signal form of the pace pulse tail 30.

The process of identifying pace pulses 10 may employ the technique disclosed in U.S. Pat. No. 4,664,116; wherein, pace pulses 10 are identified by the existence of high frequency "spikes" having narrow width and a sharp rise time, which exceed a minimum dynamic noise threshold.

Additional hardware and software can be employed to remove detected pace pulses 10. In particular, a technique is described in U.S. Pat. No. 4,832,041 in which values of the ECG signal 50 that are within a window containing the pace pulse 10 are replaced with substitute values that are an interpolation of selected values of the ECG signal 50. The substitute values form a line that is very close to what the ECG signal 50 would be if a pace pulse 10 had not occurred. However, this algorithm is not designed to eliminate the pace pulse tail 30. Unfortunately, the remaining energy of the pace pulse tail 30 may be erroneously detected as a QRS complex (heart response 40). This may cause the misdiagnosis of the patient's underlying ECG rhythm and result in a missed detection of an asystole condition.

U.S. Pat. No. 4,934,376 discloses a method and apparatus for detecting the occurrence of heartbeats in an ECG signal which may also include pacer artifacts, comprising analysis of the ECG signal for providing a heartbeat signal indicating detection of the occurrence of a heartbeat, analysis of the ECG signal for providing a pacer artifact signal indicating detection of the occurrence of a pacer artifact, analysis of the ECG signal in a manner independent from the first-mentioned analysis for determining if a portion of the ECG signal which follows detection of a pacer artifact has changes in its amplitude level which indicate the validity of the heartbeat indicating signal, and use of the result of the last-mentioned analysis to control the providing of the heartbeat indicating signal by the first-mentioned analysis.

U.S. Pat. No. 5,033,473, by the same applicant, discloses a method and apparatus for discriminating pace pulse tails 30 generated by signals discriminated from QRS complexes (heart response 40) by mathematically ascertaining that the signal following the pace pulse peak has an exponential decay. It is ascertained whether or not the waveform decays exponentially through application of a mathematical equation.

SUMMARY OF THE INVENTION

It is an object of the invention to provide a method for differentiating pace pulse tails 30 from the true heart response 40 in an ECG signal 50 waveforms.

According to the invention, the heart response 40 of the patient's ECG signal 50 is distinguished from the pace pulse 10 of the pacemaker by assessing the pace pulse tail 30 by means of determining an area A' of the negative pulse 70 of the ECG signal 50. It has been found that the area A' of the negative pulse 70 is hardly changed by the heart response 40, because the heart response 40 is substantially isoelectric, i.e., the area above and below the zero line is the same in average. Since the heart response 40 thus only contributes area portions to the pace pulse tail 30, which, on average, consist of portions of substantially equal negative and positive areas, the area A' of the negative pulse 70 is substantially the same as the area A of the pace pulse tail 30 and substantially not influenced by the heart response 40.

When the theoretical mathematical function or an approximation of a respective shape of the pace pulse tail 30 is known, an estimated mathematical function of the pace pulse tail 30 can, in most cases, be determined from the determined area A' of the negative pulse 70. By evaluating the estimated mathematical function of the pace pulse tail 30 together with the actually measured negative pulse 70 of the ECG signal 50, it can be drawn back whether the heart response 40 is superimposed to the pace pulse 10 or not. In the former case, the heart response 40 signal can be recognized and might be separated from the pace pulse 10 and further analyzed. In the latter case, the patient's heart does not react onto the pace pulse 10 and suitable consequences have to be drawn.

In case the actual pace pulse tail 30 substantially follows an exponential function, the shape of an estimated mathematical function of the pace pulse tail 30 can be derived from the area A' (see FIG. 1C) of the negative pulse 70. The area A' of the negative pulse 70 of the ECG signal 50 can be regarded as substantially equal with the area A (see FIG. 1A) of the pace pulse 30 of the pace pulse 10. The time constant T of the exponential function for the estimated mathematical function of the pace pulse tail 30 is calculated from the area A' as following:

$$A'=A=-a * T * (\exp^{-Te/T}-1) \quad (1)$$

whereby:
a represents the amplitude of the negative pulse 70 at a time T0=0 as the starting time of the pace pulse tail 30;

Te represents an "end time" of the exponential function, whereby Te is to be set in a way that the area A' of the exponential function between T0 and Te is large enough and at least covers the heart response 40;

A' represents the area of the negative pulse 70 between T0 and Te; and

T represents the time constant of the exponential function. With x=(-Te/T) and k=(a * Te/A'), the solutions of equation (1) will also be solutions of equation (2):

$$f(x)=k * [\exp(x)-1]-x=0 \quad (2)$$

Using the Adomian's method, x can be approximated as:

$$x \sim -k+k * \exp(-k)+k^2 * \exp(-2*k)+1.5 * k^3 * \exp(-3*k)+\ldots \quad (3)$$

The value of the time constant T can eventually be determined by $$T=-Te/x. \quad (4)$$

Once the estimated mathematical function of the pace pulse tail 30 is known with sufficient accuracy, the heart response 40 can be preferably detected by the following methods:

(a) Within a moving window, changes of an area between the negative pulse 70 of the ECG signal 50 and the estimated mathematical function are detected. The moving window is defined as a section of the time axis and should at least have the substantial length of a typical heart response 40. Further more, the moving window is preferably set as a multiple of superimposed periodic disturbances, such as the mains' frequency.

If the changes significantly differ from a pre-given value, it can be expected that this results from the heart response 40. If the changes do not significantly extend the pre-given value, it is feared that no heart response 40 occurred.

(b) Differences in the slopes of the negative pulse 70 of the ECG signal 50 and the estimated mathematical function are detected.

If the differences significantly differ from a pre-given value, it can be expected that they result from the heart response 40. If the changes do not significantly extend the pre-given value, it is feared that no heart response 40 occurred.

An additional criterion can be that the significant differences have to occur at least over a given period of time. Otherwise the differences—although significant in value—are not regarded as being representative for the heart response 40, but may result from side effects.

When the pacemaker is implanted to a patient, the synthetic pace pulse 10 of that respective pacemaker is set to fixed values and the shape of the pace pulse 10 only varies little. However, the shape of the pace pulse 10 might also be influenced by side effects such as movement artifacts or when the measured lead is changed. In that case, it might be required to frequently "learn" the estimated mathematical function of the pace pulse tail 30 by frequently determining the area A' of the negative pulse 70.

According to one embodiment, the shape of the heart response 40 can be approximated by a so-called signal clamping. When a main pulse 20 is detected in the ECG signal 50, the value of the ECG signal 50 measured just before that main pulse 20 occurred is maintained (e.g. as a zero value) and set as an output until the heart response 40 is recognized in the ECG signal 50. After the heart response 40 has been recognized, the ECG signal 50—or a signal derived therefrom—is given out for further evaluation of the ECG signal 50.

According to another embodiment, the shape of the heart response 40 can be approximated by subtracting the estimated mathematical function from the negative pulse 70 of the ECG signal 50, or vice versa. The thus determined heart response 40 might be deformed or distorted due to superimposed side effects or when the estimated mathematical function not fully coincides with the actual pace pulse tail 30.

BRIEF DESCRIPTION OF THE DRAWINGS

Other objects and many of the attendant advantages of the present invention will be readily appreciated and become better understood by reference to the following detailed description when considering in connection with the accompanied drawings, in which:

FIGS. 5A and 5B show one criterion to detect the heart response 40 on the ECG signal 50, the so-called area criterion;

FIG. 6 shows another criterion to detect the heart response 40 on the ECG signal 50, the so-called slope criterion.

DETAILED DESCRIPTION OF THE INVENTION

Figure 2:
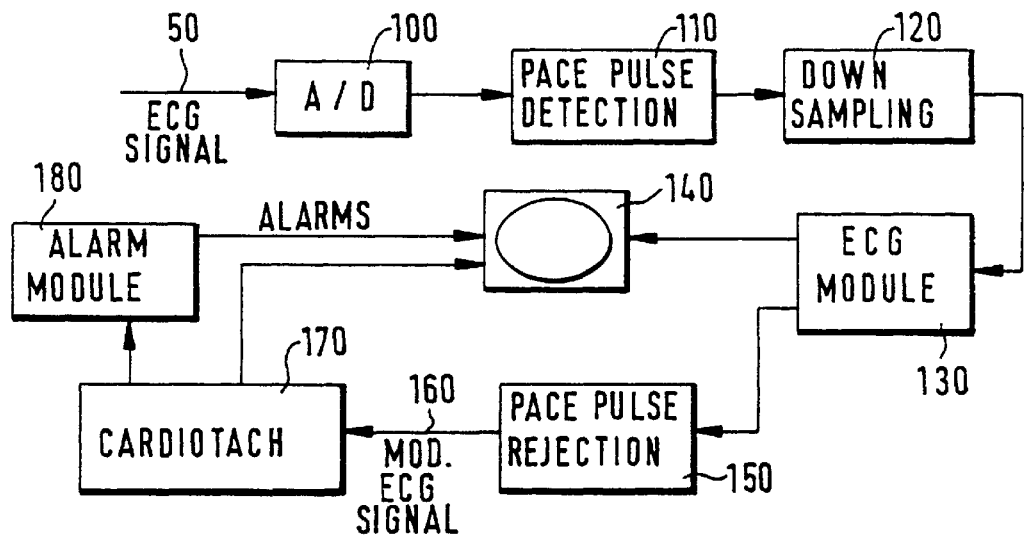
FIG. 2 shows a preferred embodiment of an ECG measurement system according to the invention.

FIG. 2 shows a preferred embodiment of an ECG measurement system according to the invention. The ECG signal 50 is sampled, e.g. with 4 kHz, by an A/D converter 100 for one or more different leads/channels. Pacemaker spikes, such as the main pulse 20, are determined in a pace pulse detection unit 110 by algorithms as known in the art. After the detection of the pacemaker spikes, the ECG signal 50 is sampled down, e.g. to 500 Hz, by a down-sampler 120 and the determined pacemaker spikes and their polarity are marked in some of the bits representing the respective measurement values of the pace pulse 10. Then the ECG signal 50 is transferred in a diagnostic bandwidth (e.g. 0.05 Hz to 130 Hz) to an ECG module 130.

The ECG module 130 applies the ECG signal 50, or a respective signal derived therefrom, to a display 140 and to a pace pulse rejection unit 150. The pace pulse rejection unit 150 applies on its output a modified ECG signal 160 to a cardiotach 170, which counts the heart rate, and to other (not shown) units which might require the modified ECG signal 160. The modified ECG signal 160 is a signal derived from the ECG signal 50, whereby the pace pulses 10 are of the ECG signal 50 are "rejected", meaning that the signals resulting from the pacemaker are more or less suppressed. In the ideal case, the modified ECG signal 160 only comprises the heart response 40. The cardiotach 170 receives the modified ECG signal 160 and thus counts the heart rate based on the QRS complexes of the heart response 40. The pace pulse rejection unit 150 might further detect whether the heart response 40 occurs and might consequently generate respective ECG alarms.

In a preferred embodiment, the cardiotach 170 signals the detected heart rate to the display 140 and generates a sound signal corresponding to the heart rate (also called QRS plop) for the display 140. The cardiotach 170 further applies a signal to an alarm module 180 which creates respective ECG alarms, e.g. to the display 140 or other units, when it is detected that no heart response 40 occurs or when other alarm situations appear.

In a first embodiment, the pace pulse rejection unit 150 performs a so-called signal clamping with the incoming ECG signal 50. When the pace pulse detection unit 110 detects a pace pulse 10 in the ECG signal 50, the modified ECG signal 160 is set to the value of the incoming ECG signal 50 measured just before the last main pulse 20 has been determined. This value is maintained as a baseline until the pace pulse rejection unit 150 recognizes the heart response 40 in the ECG signal 50. Because it may take a few milliseconds until the heart response 40 is detected, a delay line might be implemented inside the pace pulse rejection unit 150. This allows to shift back in time the point in time when the signals are released from clamping.

Figure 3A:
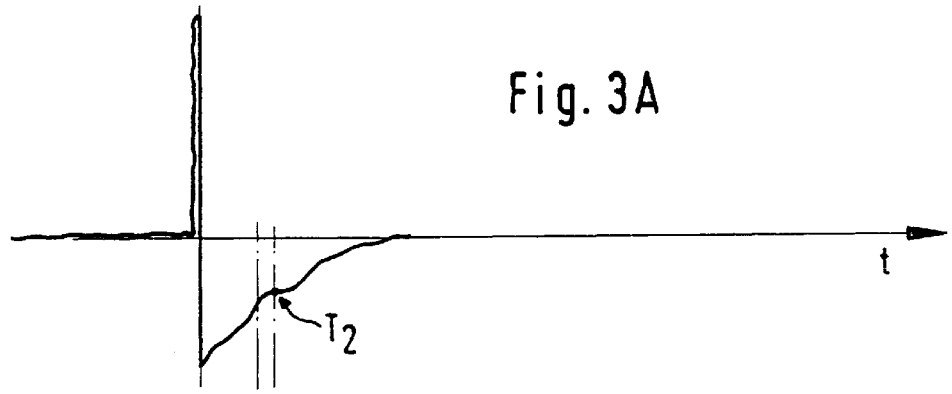
FIGS. 3A and 3B show an example for signal clamping.
Figure 3B:
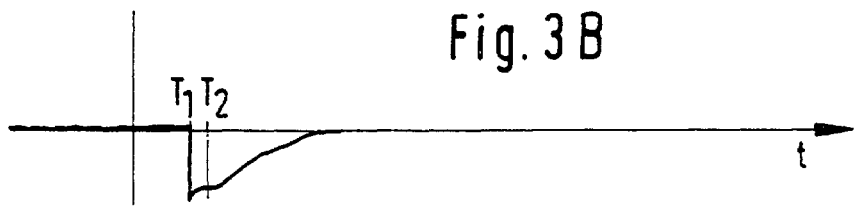

FIGS. 3A and 3B show an example for the signal clamping. In that example, the pace pulse rejection unit 150 detects the heart response 40 at a time T2 (FIG. 3A). Due to the delay line the signal clamping is terminated at T1 and the signals in FIG. 3B will go to the cardiotach 170 which will detect the heart response 40. Without any heart response 40 the clamping will continue until the signal is back to the baseline and the cardiotach 170 will not trigger on the signal.

In a second embodiment, the pace pulse rejection unit 150 performs a signal subtraction. An approximated heart response is determined by subtracting the estimated mathematical function from the negative pulse 70 of the ECG signal 50, or vice versa. The pace pulse rejection unit 150 applies the approximated heart response on its output as the modified ECG signal 160 to the cardiotach 170.

According to the invention, the pace pulse rejection unit 150 distinguishes the heart response 40 of the patient's ECG signal 50 from the pace pulse 10 of the pacemaker by determining the area A' of the negative pulse 70 of the ECG signal 50. For most of the pacemakers, particularly for unipolar pacemakers, the shape of the pace pulse tail 30 will follow an exponential decay, so that the theoretical mathematical function of the pace pulse tail 30 can be assumed as an exponential function. An estimated mathematical function of the pace pulse tail 30 can be determined from the area A' of the negative pulse 70. The time constant T of the exponential function is calculated from the initial amplitude a and the area A (which is almost equal to A') below the function between the time T0 and the time Te as set out by the given equations (1) to (4). However, other mathematical functions can also be used for that purpose, dependent on the shape of the ECG signal 50.

The shapes of the pace pulses 10 of a respective pacemaker generally only slightly vary, but might also be influenced by side effects such as movement artifacts or when the measured lead is changed. In most of the practical applications, it will therefore be required to frequently "learn" the estimated mathematical function of the pace pulse tail 30 by frequently determining the area A' of the negative pulse 70. An estimated mathematical function of the pace pulse tail 30 is then "learned", e.g. every few seconds, and compared with the actual ECG signals 50 of the following heart beats.

If a significant difference between the estimated mathematical function, which is expected to represent the "pure" pace pulse 10 of the pacemaker, and the actual ECG signals 50 is detected, the pace pulse rejection unit 150 "recognizes" the heart response 40 within the ECG signal 50. In the first embodiment, the pace pulse rejection unit 150 will then stop clamping the value of the modified ECG signal 160 and the cardiotach 170 will 'see' the heart response 40.

It has been found that, if the heart responds to the pace pulse 10 and a heart response 40 is superimposed, the area A' of the negative pulse 70 of the ECG signal 50 nearly is the same as the area A of the pace pulse tail 30. This is due to the fact that the heart response 40 is substantially isoelectric, i.e. the area above and below the zero line is the same. The calculation of the shape of the pace pulse tail 30 according to the invention can therefore be executed irrespective of whether the heart response 40 occurs or not.

Figure 4A:
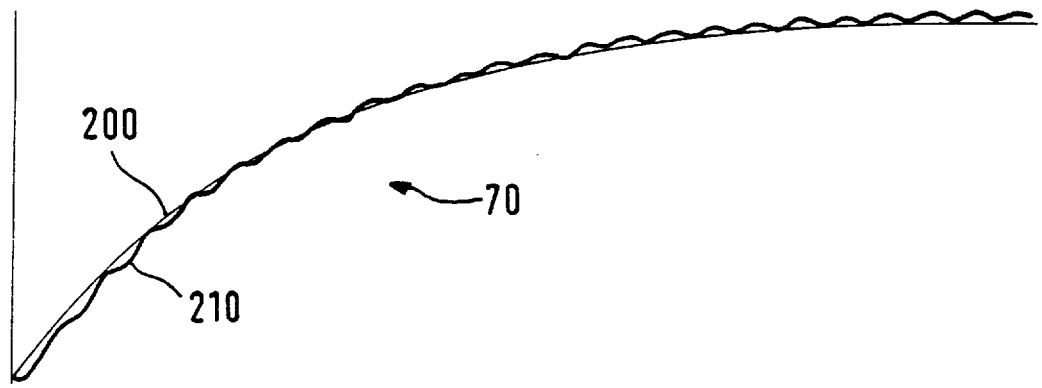
FIG. 4A shows the negative pulse 70 of the ECG signal 50 not comprising any heart response.

FIG. 4A shows the negative pulse 70 of the ECG signal 50 not comprising any heart response 40. A learned exponential function 200 and an actually measured signal 210 with a 50 Hz line frequency noise superimposed is shown.

Figure 4B:
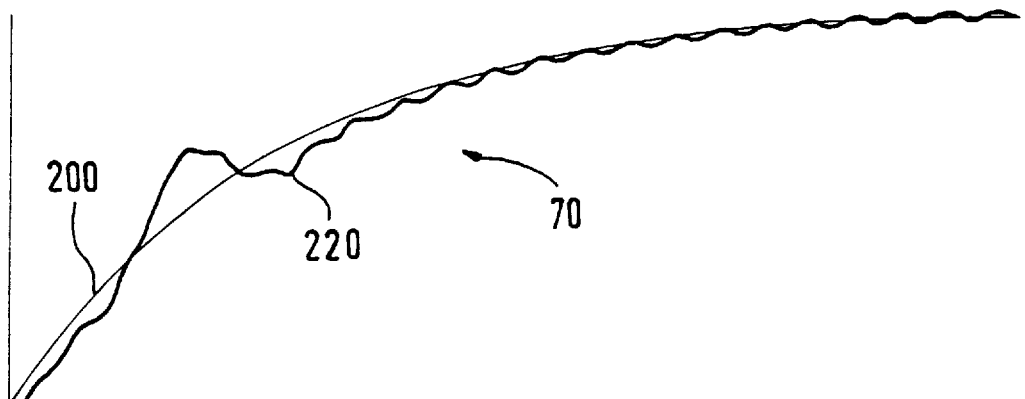
FIG. 4B shows the negative pulse 70 of the ECG signal 50 comprising the heart response 40.

FIG. 4B shows the negative pulse 70 of the ECG signal 50 comprising the heart response 40. The learned exponential function 200 and an actually measured signal 220 with a 50 Hz line frequency noise superimposed is shown.

To detect the heart response 40 in the ECG signal 50 a set of different criteria can be used. However, all of those criteria have to take into account that the estimated mathematical function might not be 100% precise, i.e. may have an offset shift versus the real pace pulse tail 30 or may have slightly imprecise values, e.g. the time constant T of the exponential function does not fully fit the pulse pace tail 30. Further more, the ECG signals 50 might have a diagnostic bandwidth and so, all kinds of noise (e.g., 50 Hz or 60 Hz power line noise, baseline wandering, artefacts etc.) have to be considered.

FIGS. 5A and 5B show one criterion to detect the heart response 40 on the ECG signal 50, the so-called area criterion. An area 250 between an actually measured ECG signal 260 and the "learned" estimated mathematical function 200 is calculated within a moving window 270 of a fixed duration in time. The moving window 270 is moved along the time axis, as indicated by arrow 280, by a predetermined speed, e.g. in real-time, i.e. the right side of the mowing window 270 represents the latest measurement value.

The size of the moving window 270, that is the lateral extension on the time axis, is preferably set out as to cover the typical width of the heart response 40 for the selected type of patient (e.g., adult, pediatric or neonatal). In that case, the size of the moving window 270 has to at least cover the main activity, i.e. the ventricular contraction or R wave, of the heart response 40. Further more, in case of superimposed periodic disturbances, e.g. the power line frequency (20 ms for 50 Hz or 16.67 ms for 60 Hz), the size of the moving window 270 is preferably set out as a multiple of the period of the periodic disturbance. If the amount of the signed area 250 within the moving window 270 changes more than a pre-given value, it is expected that this change results from the heart response 40 of the patient and that the heart response 40 can be "seen". In case that signal clamping according to the first embodiment is performed, the clamping of the negative pulse 70 is stopped and the ECG signal 50 is output as shown in FIG. 3B.

In case that no heart response 40 occurs, the area 250 within the moving window 270 does not vary much, even if there might be an offset between the actually measured ECG signal 260 and the "learned" estimated mathematical function 200 or if the time constant T is not precise.

Figure 1A:
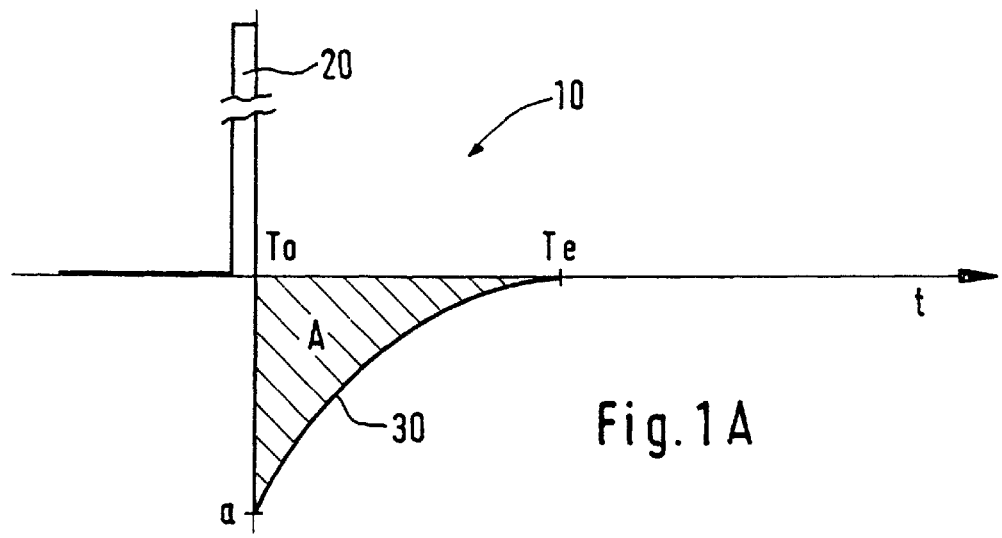
FIG. 1A shows a typical pace pulse 10 consisting of a main pulse 20 and pace pulse tail 30.
Figure 1B:
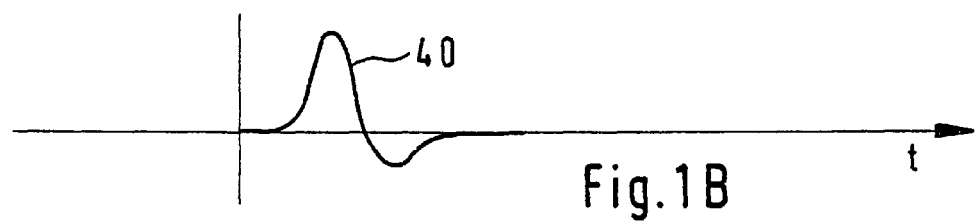
FIG. 1B shows an example of a shape of a heart response 40.
Figure 1C:
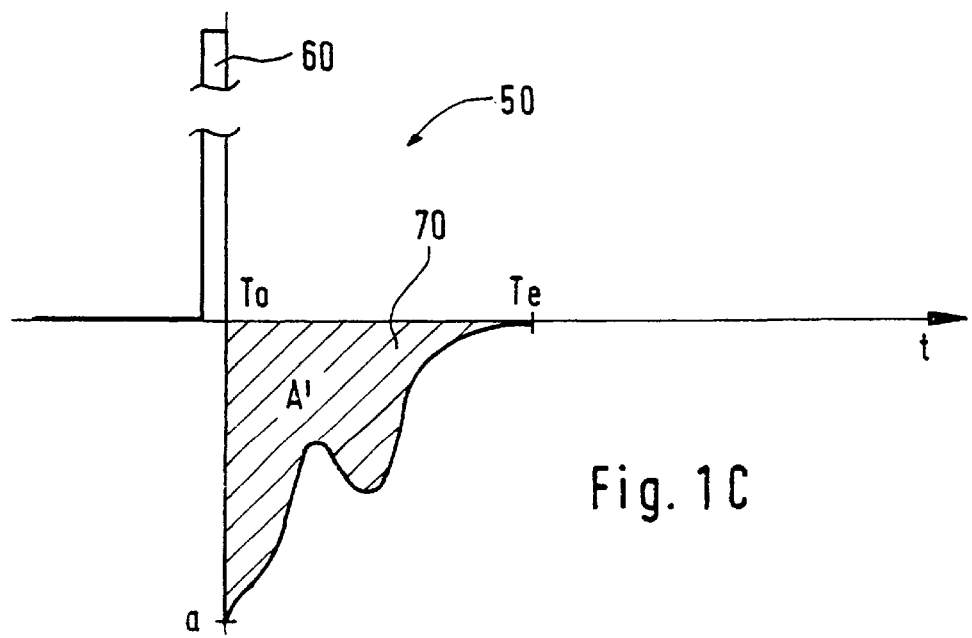
FIG. 1C shows an example of a shape of an actual ECG signal 50 which results from the pace pulse 10 superimposed with the heart response 40 of the patient.

At a time Tw, the value of area 250 is available for the first time after a respective main pulse 20 had occurred. The time Tw is determined by the beginning of the detected pace pulse tail 30 at time T0 (compare FIG. 1A) and the size of the moving window 270. If the value of the area 250 changes thereafter at least for a value "minimum delta-area" within a time "maximum delta-time", it is expected that the heart response 40 can be "seen", meaning that the heart response 40 is assumed to be present.

FIG. 6 shows another criterion to detect the heart response 40 on the ECG signal 50, the so-called slope criterion. From the beginning of the detected pace pulse tail 30 at time T0 (compare FIG. 1A), it is observed whether the slope of the actually measured ECG signal 260 differs from the slope of the "learned" estimated mathematical function for more than a pre-given slope value in any direction (positive or negative). An additional criterion can be that the slope of the actually measured ECG signal 260 differs from the slope of the "learned" estimated mathematical function for more than the pre-given slope value and over a time value longer than a pre-given time value. When the pre-given slope value is exceeded and longer than the pre-given time value, it is expected that this results from the heart response 40 of the patient and that the heart response 40 can be "seen".

In case that the actually measured ECG signal 260 might be disturbed by a periodic signal, such as the power line noise, the time value for exceeding the pre-given slope value must be larger than a quarter of the period of the disturbing signal.

In real-time systems because of possible CPU runtime constraints, the time constant T of the exponential function is preferably not calculated mathematically at runtime, but is derived from a constant table. The constant table, e.g. a constant file, preferably contains a matrix of normalized area values A for different values of Te and different values of T.

The pace pulse rejection unit 150 preferably searches into the constant table for an area value A* which is higher and an area value A which is lower than the measured area value A'. The pace pulse rejection unit 150** then calculates the T value of the measured area A' by a linear interpolation of the T values belonging to the area values A* and A**.

In a preferred embodiment, the exponential function is not calculated by means of a mathematical function, e.g. by library function calls or by calculating the first elements of a mathematical progression. Due to possible CPU runtime constraints, the pace pulse rejection unit 150 calculates each new value $e_n$ of the exponential function from the previous one $e_{n-1}$ by the equation:

$$e_n = c_i * e_{n-1}, \quad (5)$$

whereby $c_i$ is a constant dependent on the time constant T of the exponential function, and the values $e_n, e_{n-1}, e_{n-2}, \ldots$ of the exponential function are equidistant in time. The constant $c_i$ is preferably taken up from a lookup table (e.g. a constant file).

The "end time" Te for the area calculation is preferably set when the ECG signal 50 is close to the baseline for a specific time. However, Te should not be too short, because of imprecise T values, and not too long, because a false T value might then be determined if artefacts occur in the ECG signal 50.

The pace pulse rejection unit 150 comprises suitable means for determining the area A' of the negative pulse 70, for determining an estimated mathematical function from the determined area A', and for evaluating the estimated mathematical function 200 together with the ECG signal 50. The means for evaluating the estimated mathematical function together with the ECG signal preferably preferably comprises either means for determining the enclosed area 250 between the ECG signal 260 and the estimated mathematical function 200 within the moving window 270, or means for determining a slope of the ECG signal 260 at a certain moment in time. In the latter case, the pace pulse rejection unit 150 further comprises means for determining a slope of the estimated mathematical function 200 at that certain moment in time, and means for comparing the determined slope of the ECG signal 260 with the determined slope of the estimated mathematical function 200 at that certain moment in time. Another preferred embodiment further comprises means for detecting a main pulse 20 and means for setting the modified ECG signal 160 at a value of the ECG signal 50 measured just before that main pulse 20 occurred, until the heart response 40 is recognized in the ECG signal 50. All those means are preferably implemented by suitable electronic circuits (hardware), by respective software modules, or combinations thereof.

I claim:

1. A system for detecting a heart response in an ECG signal of a patient, the patient having a pacemaker emitting a pace pulse, the system comprising:

means for measuring an ECG signal of said patient in response to an applied pace pulse having a main pulse and a tail component, said ECG signal also having a main pulse and a tail component, means for determining an area of the tail component of the ECG signal, means for determining an estimated mathematical function describing a characteristic of at least a portion of the tail component of the ECG signal from the determined area of the tail component, and means for detecting the heart response by evaluating the estimated mathematical function together with the ECG signal.

2. The system according to claim 1, wherein the means for detecting the heart response by evaluating the estimated mathematical function together with the ECG signal comprises:

means for determining an enclosed area between the ECG signal and the estimated mathematical function within a pregiven window.

3. The system according to claim 1, wherein the means for evaluating the estimated mathematical function together with the ECG signal comprises:

means for determining a slope of the tail component of the ECG signal at a certain moment in time, means for determining a slope of the estimated mathematical function at the certain moment in time, and means for comparing the determined slope of the tail component of the ECG signal with the determined slope of the estimated mathematical function at the certain moment in time.

4. The system according to claim 1, further comprising:
means for detecting the main pulse in the ECG signal, and
means responsive to detection of said main pulse by said means for detecting for setting a reference value at a value of the ECG signal measured by the means for measuring just before occurrence of the main pulse the reference value used as a zero value for the heart response recognized in the tail component of the ECG signal.

5. The system according to claim 1, wherein the
means for detecting detects a main pulse in the ECG signal, and
determines a shape of the heart response by subtracting the estimated mathematical function from the tail component of the ECG signal.

6. The system according to claim 1,
wherein the means for detecting further generates a modified ECG signal by suppressing the main pulse within the ECG signal, and
a cardiotach for counting a heart rate of the patient from the modified ECG signal.

7. A method for detecting a heart response in an ECG signal of a patient, the patient having a pacemaker emitting a pace pulse, comprising the steps of:

measuring an ECG signal of the patient in response to an applied pace pulse having a main pulse and a tail component, said ECG signal also having a main pulse and a tail component, determining an area of the tail component of the ECG signal, determining an estimated mathematical function describing a characteristic of at least a portion of the tail component of the ECG signal from the determined area, and detecting the heart response by evaluating the estimated mathematical function together with the ECG signal.

8. The method according to claim 7, wherein the evaluating the estimated mathematical function together with the ECG signal comprises a step of:

determining an enclosed area between the tail component of the ECG signal and the estimated mathematical function within a pregiven window.

9. The method according to claim 7, wherein the step of detecting the heart response by evaluating the estimated mathematical function together with the ECG signal comprises a step of:

determining a slope of the tail component of the ECG signal at a certain moment in time, determining a slope of the estimated mathematical function at the certain moment in time, and comparing the determined slope of the tail component of the ECG signal with the determined slope of the estimated mathematical function at the certain moment in time.

10. The method according to claim 7, further comprising steps of:

detecting said main pulse in the ECG signal, and setting a reference value in response to the detecting of said main pulse, at a value of the ECG signal measured just before occurrence of the main pulse and using the reference value as a zero value for the heart response recognized in the ECG signal.

11. The method according to claim 7, further comprising steps of:

detecting a main pulse in the ECG signal, and determining a shape of the heart response by subtracting the estimated mathematical function from the tail component of the ECG signal.

12. The method according to claim 7, wherein the detecting step further generates a modified ECG signal by suppressing said main pulse within the ECG signal, and counting a heart rate of the patient from the modified ECG signal.

* * * * *